United States Patent
Rumoro

(10) Patent No.: US 11,646,105 B2
(45) Date of Patent: May 9, 2023

(54) PATIENT PREDICTIVE ADMISSION, DISCHARGE, AND MONITORING TOOL

(71) Applicant: RUSH UNIVERSITY MEDICAL CENTER, Chicago, IL (US)

(72) Inventor: Dino Peter Rumoro, Winfield, IL (US)

(73) Assignee: Rush University Medical Center, Chicago, IL (US)

( * ) Notice: Subject to any disclaimer, the term of this patent is extended or adjusted under 35 U.S.C. 154(b) by 345 days.

(21) Appl. No.: 16/490,815

(22) PCT Filed: Mar. 2, 2018

(86) PCT No.: PCT/US2018/020597
§ 371 (c)(1),
(2) Date: Sep. 3, 2019

(87) PCT Pub. No.: WO2018/160929
PCT Pub. Date: Sep. 7, 2018

(65) Prior Publication Data
US 2020/0013490 A1    Jan. 9, 2020

Related U.S. Application Data

(60) Provisional application No. 62/466,974, filed on Mar. 3, 2017.

(51) Int. Cl.
G16H 10/60 (2018.01)
G06F 16/23 (2019.01)

(52) U.S. Cl.
CPC ......... G16H 10/60 (2018.01); G06F 16/2365 (2019.01)

(58) Field of Classification Search
CPC ........ G16H 50/20; G16H 50/70; G16H 50/30; G16H 15/00; G16H 10/60; G16H 50/50; G16H 40/20
See application file for complete search history.

(56) References Cited

U.S. PATENT DOCUMENTS

2003/0101076 A1*  5/2003  Zaleski ................. G16H 15/00
                                                     705/2
2007/0150307 A1   6/2007  Lancaster et al.
(Continued)

OTHER PUBLICATIONS

M. Gowsalya, K. Krushitha and C. Valliyammai, "Predicting the risk of readmission of diabetic patients using MapReduce," 2014 Sixth International Conference on Advanced Computing (ICoAC), 2014, pp. 297-301 (Year: 2014).*

(Continued)

Primary Examiner — Joseph D Burgess
(74) Attorney, Agent, or Firm — Barnes & Thornburg LLP

(57) ABSTRACT

Predictions can be provided for admission, discharge, pathway, and units for a patient during a stay at a healthcare facility. In some aspects, a computing device receives initial data regarding the patient and generates an admission or discharge prediction indicating a probability that the patient will be admitted to or discharged from the healthcare facility. The computing device segments portions of the initial data into segmented data and stores the segmented data in one or more of a plurality of segmentation categories. The computing device compares the segmented data to one or more patterns of a predictive model and, based on the comparing, generates a total length-of-stay (LOS) prediction indicating a duration of time for which the patient will stay at the healthcare facility.

24 Claims, 12 Drawing Sheets

(56) References Cited

U.S. PATENT DOCUMENTS

| | | | |
|---|---|---|---|
| 2009/0105550 A1 | 4/2009 | Rothman et al. | |
| 2011/0245630 A1* | 10/2011 | St. Pierre | G16H 15/00 |
| | | | 600/301 |
| 2011/0295622 A1* | 12/2011 | Farooq | G16H 50/70 |
| | | | 705/3 |
| 2012/0116180 A1* | 5/2012 | Rothman | G16H 50/70 |
| | | | 600/300 |
| 2012/0232926 A1 | 9/2012 | Boyle et al. | |
| 2012/0271612 A1* | 10/2012 | Barsoum | G16H 50/30 |
| | | | 703/11 |
| 2014/0108033 A1* | 4/2014 | Akbay | G16Z 99/00 |
| | | | 705/2 |
| 2015/0025329 A1* | 1/2015 | Amarasingham | G16H 50/20 |
| | | | 600/300 |

OTHER PUBLICATIONS

E. AbuKhousa and P. Campbell, "Predictive data mining to support clinical decisions: An overview of heart disease prediction systems," 2012 International Conference on Innovations in Information Technology (IIT), 2012, pp. 267-272, doi: 10.1109/INNOVATIONS. 2012.6207745. (Year: 2012).*

International Search Report and International Preliminary Report on Patentability regarding International Application No. PCT/US2018/020597 dated May 4, 2018, 9 pages.

\* cited by examiner

PATIENT PREDICTIVE ADMISSION, DISCHARGE, AND MONITORING TOOL

RELATED APPLICATIONS

The present application is a National Stage of PCT/US2018/020587, filed Mar. 2, 2018, which claims the benefit of priority to U.S. Provisional Patent Application No. 62/466,974, filed on Mar. 3, 2017, and entitled "PATIENT PREDICTIVE ADMISSION, DISCHARGE, AND MONITORING TOOL," both of which are hereby incorporated by reference in their entireties.

BACKGROUND

The subject technology is generally directed to computer-implemented planning and prediction of a patient stay at a healthcare facility for efficient administration of patient care.

Patients can be admitted to a healthcare facility (e.g., hospital) by one of a variety of means, such as delivery by emergency medical service ("EMS"), walk-in, transfer-in, or scheduled outpatient arrival. A sudden influx of unanticipated patients can cause strain on the resources and capacity of a hospital. Inefficient operation of a health care facility can lead to excessively long or excessively short patient length of stay as well as increased hospital operating expenses.

SUMMARY

The subject technology is illustrated, for example, according to various aspects described below.

A system for storing electronic data can include: one or more processors; a raw patient database; a normalized and categorized patient database; a prediction database; a user interface; and a memory comprising instructions. When executed by one or more processors, the instructions can cause the one or more processors to: receive initial patient data; store the initial patient data in the raw patient database; extract, from the initial patient data, initial categorized patient data relating to one or more conditions of a patient upon arrival to a first unit of a healthcare facility; store the initial categorized patient data in the normalized and categorized patient database; after storing the initial categorized patient data in the normalized and categorized patient database, delete the initial patient data from the raw patient database; based on the initial categorized patient data, generate a first prediction comprising a predicted characteristic of a patient stay at the first unit; store the first prediction in the prediction database; receive additional patient data based on the patient stay at the first unit; store the additional patient data in the raw patient database; extract, from the additional patient data, additional categorized patient data relating to one or more conditions of the patient upon discharge from the first unit; store the additional categorized patient data in the normalized and categorized patient database; after storing the additional categorized patient data in the normalized and categorized patient database, delete the additional patient data from the raw patient database; segment portions of the initial categorized patient data and the additional categorized patient data into segmented data, wherein the segmented data comprises a plurality of time series, wherein each of the time series comprises a plurality of indicators for a condition of the patient across a period of time; based on the segmented data, generate a second prediction comprising a predicted characteristic of a patient stay at a second unit of the healthcare facility; and/or store the second prediction in the prediction database.

A method for storing electronic data can include: receiving initial patient data; storing the initial patient data in a raw patient database; extracting, from the initial patient data, initial categorized patient data relating to one or more conditions of a patient upon arrival to a first unit of a healthcare facility; storing the initial categorized patient data in a normalized and categorized patient database; after storing the initial categorized patient data in a normalized and categorized patient database, deleting the initial patient data; based on the initial categorized patient data, generating a first prediction comprising a predicted characteristic of a patient stay at the first unit; storing the first prediction in a prediction database; receiving additional patient data based on the patient stay at the first unit; storing the initial patient data in the raw patient database; extracting, from the additional patient data, additional categorized patient data relating to one or more conditions of the patient upon discharge from the first unit; storing the additional categorized patient data in a normalized and categorized patient database; after storing the additional categorized patient data in a normalized and categorized patient database, deleting the additional patient data; segmenting portions of the initial categorized patient data and the additional categorized patient data into segmented data, wherein the segmented data comprises a plurality of time series, wherein each of the time series comprises a plurality of indicators for a condition of the patient across a period of time; based on the segmented data, generating a second prediction comprising a predicted characteristic of a patient stay at a second unit of the healthcare facility; and/or storing the second prediction in the prediction database.

A non-transitory computer-readable medium can include instructions for storing electronic data. When executed by one or more computers, the instructions can cause the one or more computers to: receive initial patient data; store the initial patient data in a raw patient database; extract, from the initial patient data, initial categorized patient data relating to one or more conditions of a patient upon arrival to a first unit of a healthcare facility; store the initial categorized patient data in the normalized and categorized patient database; after storing the initial categorized patient data in the normalized and categorized patient database, delete the initial patient data from the raw patient database; based on the initial categorized patient data, generate a first prediction comprising a predicted characteristic of a patient stay at the first unit; store the first prediction in a prediction database; receive additional patient data based on the patient stay at the first unit; store the additional patient data in the raw patient database; extract, from the additional patient data, additional categorized patient data relating to one or more conditions of the patient upon discharge from the first unit; store the additional categorized patient data in the normalized and categorized patient database; after storing the additional categorized patient data in the normalized and categorized patient database, delete the additional patient data from the raw patient database; segment portions of the initial categorized patient data and the additional categorized patient data into segmented data, wherein the segmented data comprises a plurality of time series, wherein each of the time series comprises a plurality of indicators for a condition of the patient across a period of time; based on the segmented data, generate a second prediction comprising a predicted characteristic of a patient stay at a second unit of the healthcare facility; and/or store the second prediction in the prediction database.

Generating the second prediction can include comparing the segmented data to one or more patterns of a predictive model. The characteristic of the patient stay at the first unit can include an admit to the second unit prediction, a discharge prediction, a length-of stay in the first unit prediction. The characteristic of the patient stay at the second unit can include a length-of-stay in the second unit prediction, and/or a final disposition prediction. The condition of the patient can include arrival location, clinical condition, and/or demographics data. Generating the second prediction can include: comparing the segmented data to patterns of a plurality of predictive models; combining results of the comparing with majority or weighted voting or statistical combination. The instructions, when executed by one or more processors, can cause the one or more processors to: after receiving the initial data, receive temporal data comprising variables relating to the patient; transform the temporal data into transformed data; and store the transformed data in one or more of a plurality of pattern categories. The transforming can include: converting a variable of the temporal data into a categorical variable; changing a scale or orientation of the variable; combining multiple variables of the temporal data; and transforming a coordinate system of the temporal data.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

It is to be understood that both the foregoing general description and the following detailed description are exemplary and explanatory and are intended to provide further explanation of the subject technology as claimed.

BRIEF DESCRIPTION OF THE DRAWINGS

The accompanying drawings, which are included to provide further understanding of the subject technology and are incorporated in and constitute a part of this description, illustrate aspects of the subject technology and, together with the specification, serve to explain principles of the subject technology.

DETAILED DESCRIPTION

Figure 1:
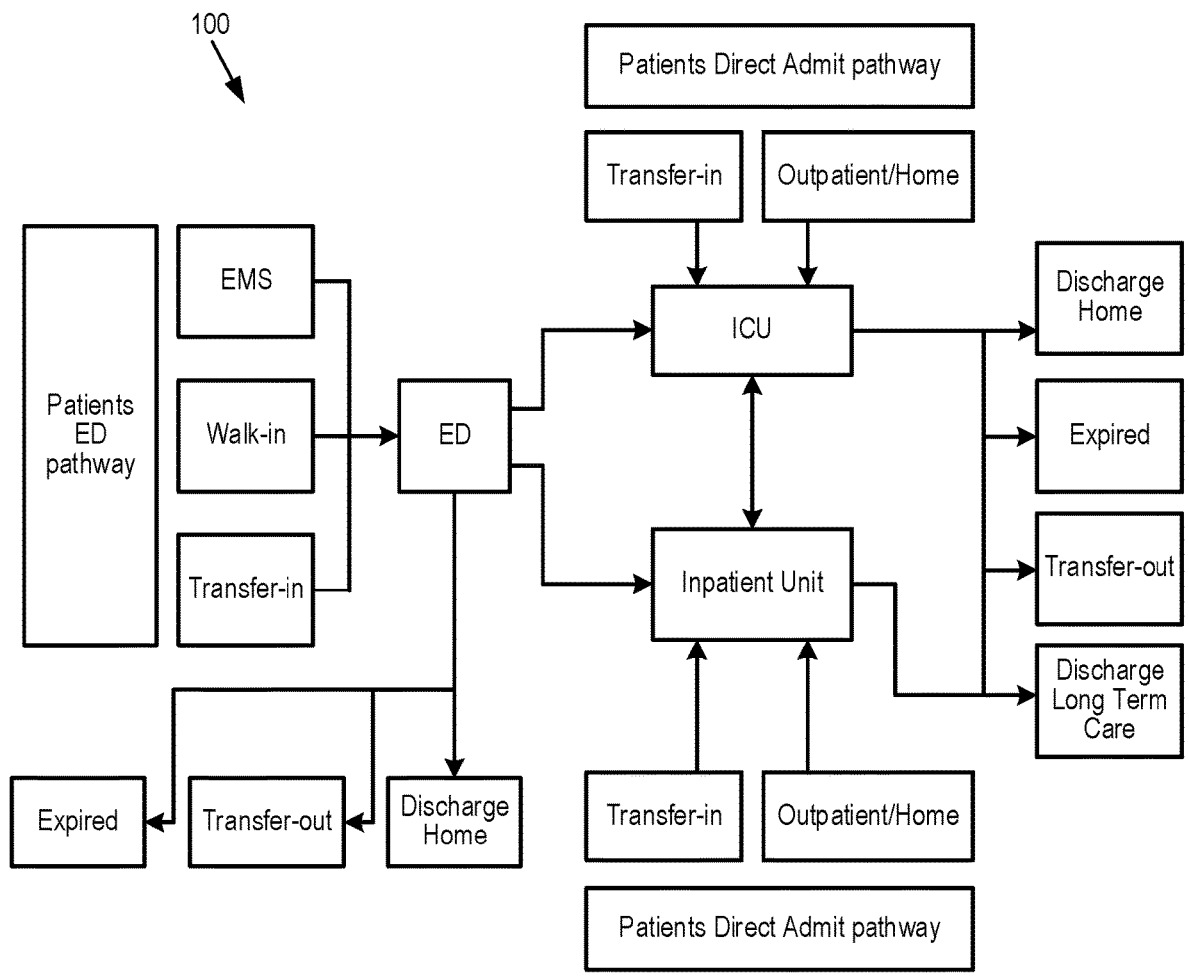
FIG. 1 illustrates an example pathway of a patient stay at a hospital, according to some embodiments of the subject technology.

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, it will be clear and apparent that the subject technology is not limited to the specific details set forth herein and may be practiced without these specific details. In some instances, certain structures and components are shown in block diagram form in order to avoid obscuring the concepts of the subject technology.

The subject technology, in some embodiments, implements predictive analytics for operational efficiencies. The subject technology, in some embodiments, includes a tool for predicting admission from an emergency department ("ED") and the final disposition from the unit along with the overall duration of the stay. The subject technology, in some embodiments, a tool to monitor the entire patient stay throughout the ED and unit. Aspects of the subject technology can facilitate admission prediction from the ED to the inpatient setting, movement within the inpatient setting (e.g., along with duration of stay, final disposition location, and overall inpatient length-of-stay), and active reporting using user interfaces.

For example, some of the techniques described herein may be used, among other things, to assimilate relevant data from multiple clinical sources to determine if a defined set of criteria are met for a patient's condition. The data may be used to determine a probability that the patient will be admitted to a hospital, develop a certain other condition, require a certain treatment, etc. Computing device(s) implementing the subject technology may also recommend certain treatments (e.g. to prescribe a first medication or not to prescribe a second medication) based on the assimilated data.

The subject technology can be implemented as a computer-implemented method, a computer system, or a non-transitory computer-readable medium including instruction (e.g., software code). The subject technology can be implemented on one or more computing devices. A computing device can include a server, a data repository, a database, a laptop computer, a desktop computer, a netbook, a mobile phone, a tablet computer, a personal digital music player, a personal digital assistant (PDA), etc. The application of one or more computing devices allows for efficient collection, analysis, and communication of patient statuses, predications, assignments, and dispositions. For example, computing devices, as described further herein, can perform functions that have been previously performed manually by medical personnel.

The subject technology can be implemented during a patient visit to a healthcare facility, such as an emergency department ("ED"). Data relating to the patient is collected, and a prediction relating to admission and/or discharge of a patient is made based on certain data. Predictions can also include a determined duration of stay overall, a determined duration of stay in each of a plurality of units, and/or a determined next unit location. The subject technology can be implemented to further analyze new data to enhance its predictive capabilities as the new data is entered. Once the prediction includes an indicator that is above a threshold for admission, the patient is listed as "Predicted Admission."

Prediction analysis can be performed, for example, by a combination of linear and logistic regression statistics for data analysis to code variables into categories after which the categories are converted into binary classifiers to predict whether or not a patient should be admitted to the hospital. While emergency departments can account for a significant percent of admissions to a hospital, these admissions are unplanned and can disrupt hospital operations and planned admissions (i.e., from the operating rooms). The subject technology can be implemented to begin the process of finding an inpatient bed for emergency department patients early in the duration of an emergency department visit. Accommodations to admit the patient can be reserved and arranged even before the emergency physician has completed their evaluation and treatment and decided to admit the patient, thereby allowing the patient to be transferred promptly to the hospital for an inpatient stay. Accordingly, the ED can maintain efficient patient throughput and decrease the number of patients who leave before treatment. The hospital can also efficiently move patients through the system, keeping beds occupied and maximizing staff efficiency.

Accordingly, the subject technology includes systems and methods that can be implemented to improve the patient experience, plan for efficient and timely movement to point of discharge, and advance the quality of care delivered. Additionally, the subject technology includes systems and methods that can improve hospital operations/finances by providing real-time optimization of patient throughput (bed turnover), decrease backlogs in ERJOR, maximize staffing and resource utilization, and decrease operational costs to enhance net income.

The subject technology, in some implementations, relates to a real-time, scalable, automated, knowledge-based disease detection and diagnosis system. The subject technology, in some implementations, includes conducting real-time (e.g., immediate, within one minute, within ten minutes, within one hour, etc., or without any intentional delay) analysis of multiple pre-diagnostic parameters received from electronic medical records as they are routinely documented as part of a clinical encounter. Some implementations of the subject technology can be utilized at any location where a patient seeks treatment (e.g., emergency departments, doctors' offices, clinics, etc.). The data being analyzed in some implementations of the subject technology may include, among other things, chief complaints, history and physical examination notes, nursing and physician notes, other provider notes, radiology dictated reports or laboratory test results. The subject technology, according to some implementations, is able to analyze discreet variables from "check boxes" as well as "pull down" menus and has a robust natural language processor to analyze free-text entries including comments of negation. The natural language processor can operate based on a library of terms, such as the national library of medicine. Other libraries can be applied according to fields, languages, etc.

As used herein, the term "real-time" is a term of art that is understood to mean occurring without any intentional delay after an entry of a command or a triggering occurrence. For example, a command that is executed in real-time after a mouse click can be executed without any intentional delay after the mouse click, for example, within one second, ten seconds, one minute, ten minutes, one hour, etc., of the mouse click.

Figure 2:
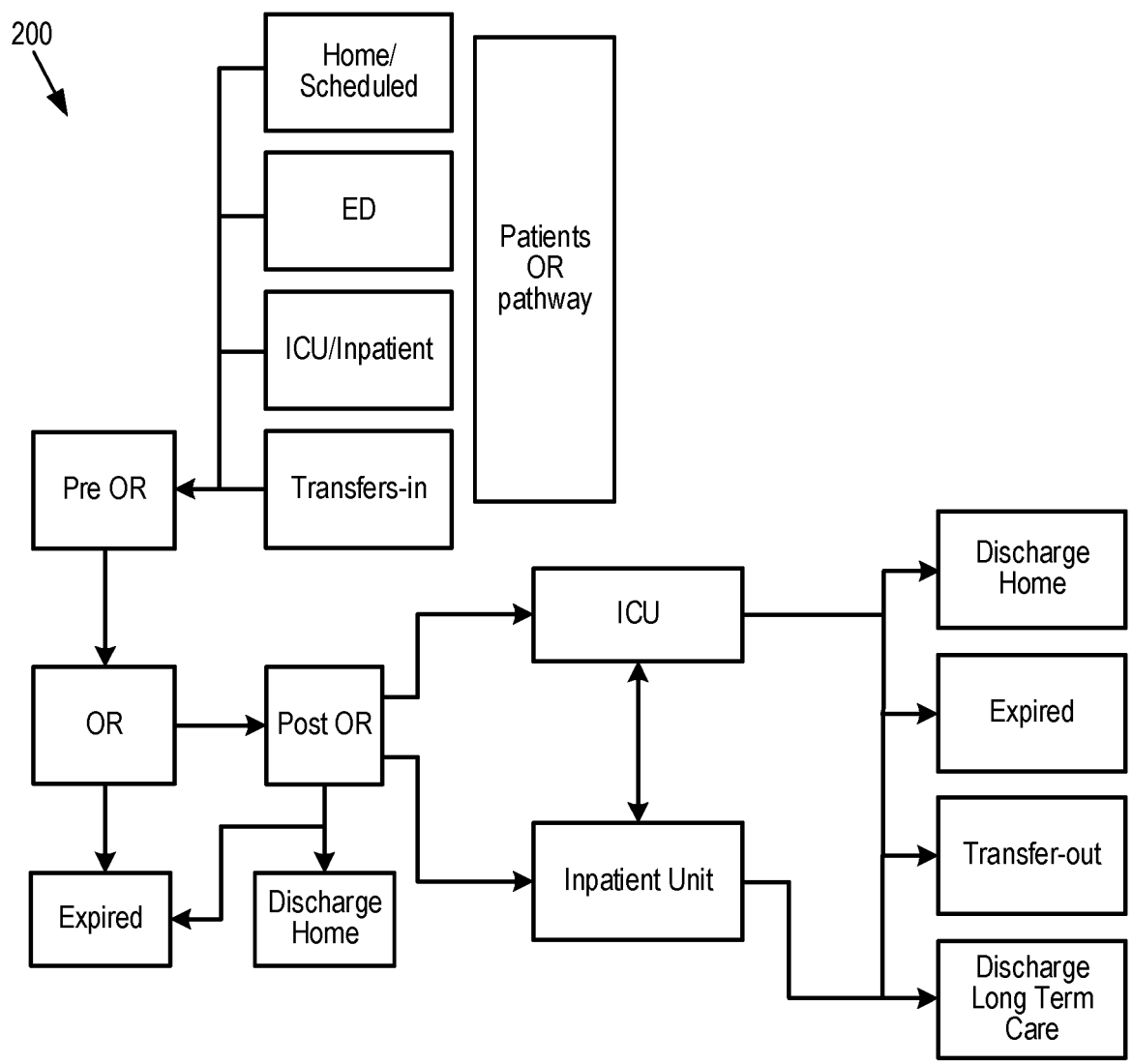
FIG. 2 illustrates an example pathway of a patient stay at a hospital, according to some embodiments of the subject technology.

A patient can experience a stay at a hospital that includes visits to various departments within the hospital, each visit lasting for a duration of time. FIGS. 1 and 2 show pathways 100 and 200 of a patient stay at a hospital. As shown, a patient pathway can be initiated with delivery by emergency medical service ("EMS"), walk-in, transfer in, or scheduled outpatient arrival. The pathway can include visits to an emergency department ("ED"), an intensive care unit ("ICU"), an inpatient unit, and/or an operating room. The pathway can include or terminate in discharge to home, expiration, transfer-out, or discharge to long term care. As can be seen, a pathway can include one of a variety of initiations, admissions, and terminations. The subject technology can be implemented during the patient visit to a healthcare facility to accurately predict some or all of a pathway of the patient, thereby allowing the healthcare facility to plan and accommodate the stages of the patient stay, as well as the stays of other patients.

Figure 3:
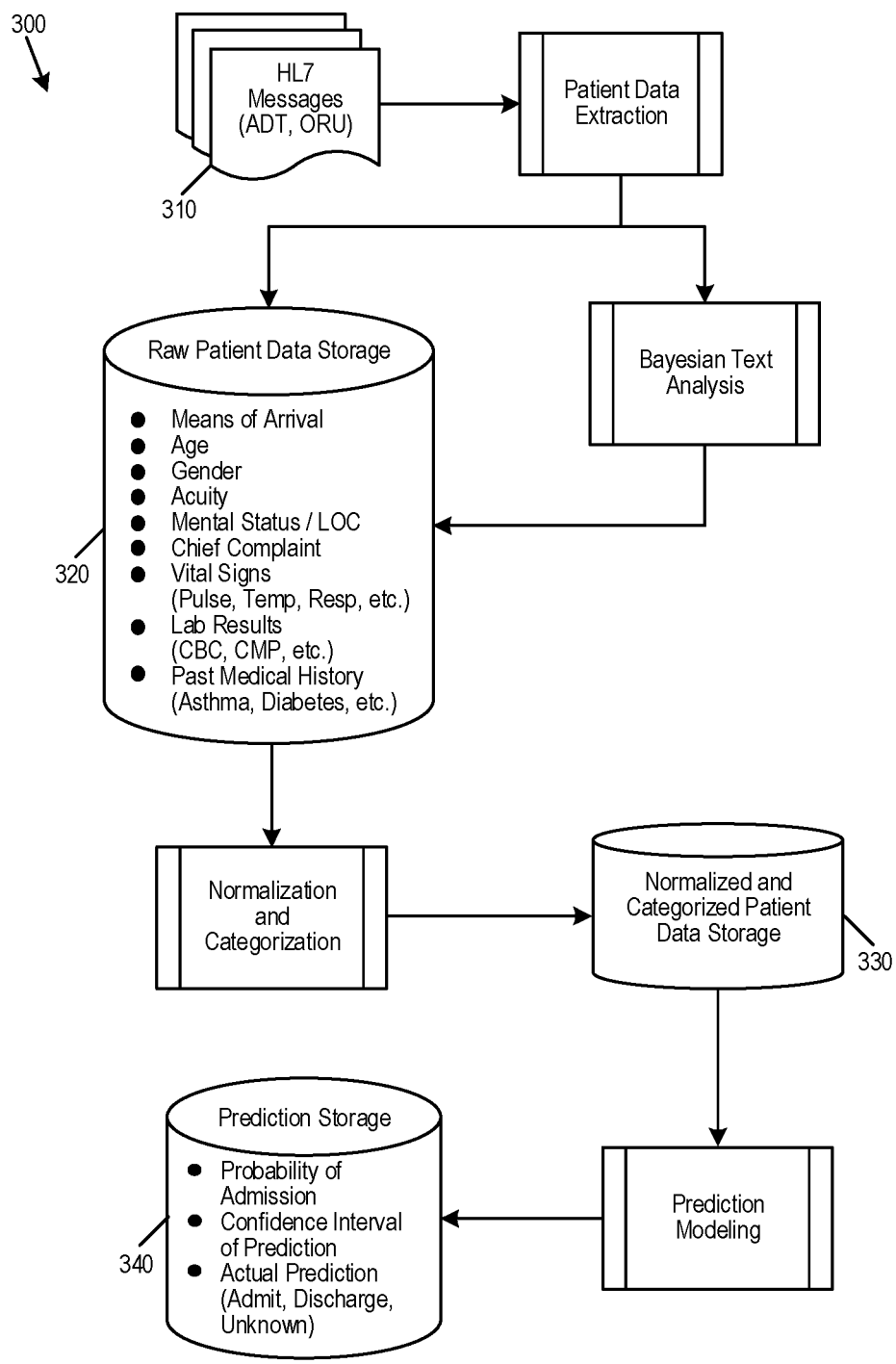
FIG. 3 illustrates an example workflow of a prediction model system for storing and analyzing data following entry of patient data, according to some embodiments of the subject technology.

The subject technology, in some embodiments, can operate based on a workflow for storing and analyzing data following entry of patient data. For example, FIG. 3 shows a workflow 300 for a prediction model system in which some examples of the subject technology can be implemented. Each of the cylinders (e.g., raw patient database 320, normalized and categorized patient database 330, and prediction database 340) can represent a data store (e.g., a table or set of related tables within a structured database). Each of the boxes connecting to the cylinders can represent an operation implemented in code which processes inputs (either from a data store or the outputs of another operation) and generates outputs. The stack of pages (e.g., incoming messages 310) can represent data being received from external systems (e.g., an EMR).

The prediction model system can receive incoming messages 310 (e.g., Health Level 7 ("HL7") messages) and process data for analysis and storage. The messages can include, for example, admission, discharge and transfer ("ADT") messages from an EMR and/or unsolicited transmission of an observation ("ORU") messages. The messages can be received, for example, by a Transmission Control Protocol ("TCP") server that listens on one or more specific ports for the incoming messages. A message processor can convert all of the information from the incoming messages into an internal format and manages any links between different messages (e.g., multiple messages for the same patient, a lab order and its associated results, a very large message broken into multiple smaller messages, etc.). Patient data is extracted from the messages 310 and stored in raw patient database 320. The extracted data can be interpreted with Bayesian text analysis prior to storage. The patient data can include, for example, means of arrival, age, gender, acuity, mental status, level of consciousness, chief complaint, vital signs, (pulse, temperature, response, etc.), lab results (CBC, CMP, etc.), and/or past medical history (asthma, diabetes, etc.).

The patient data stored in the raw patient database 320 can be normalized and/or categorized. The results of the normalization and/or categorization can be stored in normalized and categorized patient database 330. The patient data can also be analyzed for predicting characteristics of a patient pathway during the hospital stay. The characteristics can include probability of admission, confidence interval of prediction, and/or actual prediction (admit, discharge, unknown). The results of the prediction modeling can be stored in prediction database 340. Additional details regarding prediction generation are described below.

According to some embodiments, each of the raw patient database 320, the normalized and categorized patient database 330, and the prediction database 340 can be separate data stores to facilitate different processing of the data contained therein. As shown in FIG. 3, raw messages are stored as they arrive from the EMR in incoming messages 310. The data that is used during the workflow 300 can be extracted out of the messages and stored in a different format in raw patient database 320. The data stored in the raw patient database 320 can be converted, categorized, and/or normalized. For example, a metric (e.g. "temperature of 104° F.") can be converted into one of a variety of indicators (e.g., "high fever"), which is stored in normalized and categorized patient database 330. The prediction operations are applied to the converted data and to output a prediction for each patient. For example, a new prediction can be generated each time new data arrives. The prediction and its associated data are stored in the prediction database 340. The data in the incoming messages 310 and the raw patient database 320 can be deleted once each has been processed and/or stored in subsequent database, but the data in the normalized and categorized patient database 330 can be preserved throughout the patient's stay.

In some implementations of the subject technology, computing device(s) analyze the data in real-time, meaning the data is entered into the system and analyzed without intentional delay, for example, within one minute, one hour, one day, or two days of the patient being seen. The subject technology, in some embodiments, conducts real-time analysis of multiple pre-diagnostic parameters from records already being collected within an emergency department (or other treatment facility), such as triage chief complaints, physician exam notes, and test orders and results. The computing device(s), in some embodiments, can send alerts mobile devices (e.g., pagers, mobile phones, and the like) of hospital personnel notifying the physicians of possible or confirmed needs for accommodations when they are identified (e.g., within one minute of identification).

Figure 4:
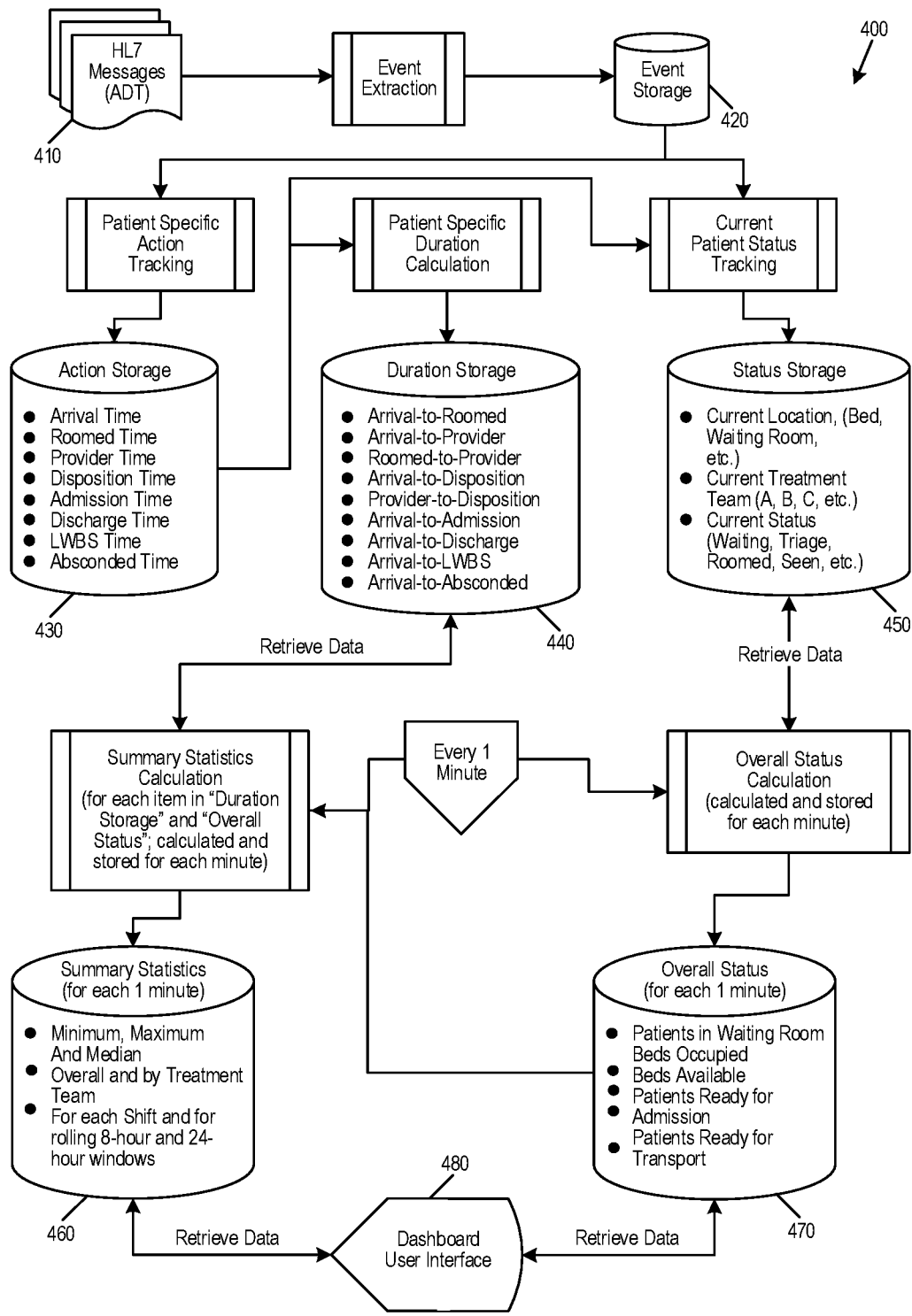
FIG. 4 illustrates an example workflow of a prediction model system for storing and analyzing data following a patient event, according to some embodiments of the subject technology.

The subject technology, in some embodiments, can operate based on a workflow for storing and analyzing data. For example, FIG. 4 shows a workflow 400 for a prediction model system in which some examples of the subject technology can be implemented. Each of the cylinders (e.g., event database 420, action database 430, duration database 440, patient status database 450, summary statistics database 460, and overall status database 470) can represent a data store (e.g., a table or set of related tables within a structured database). Each of the boxes connecting to the cylinders can represent an operation implemented in code which processes inputs (either from a data store or the outputs of another operation) and generates outputs. The stack of pages (e.g., incoming messages 410) can represent data being received from external systems (e.g., an EMR).

The prediction model system can receive incoming messages 410 (e.g., HL7 messages) and process data for analysis and storage following an event. The messages can include, for example, ADT messages from an EMR. Event data is extracted from the messages 410 and stored in event database 420. Event data can include, for example, patient identification, arrival data, transfer data, room assignment, disposition, admission data, etc.

The format of the incoming messages 310 and the incoming message 410 can be the same or similar. The data contained within the incoming messages 310 and the incoming message 410 can be different. In the workflow 300, the process of extracting data from the incoming messages 310 can include extracting data important for predicting admission (e.g., mode of arrival, demographics, vital signs, past medical history, etc.) for storage in the raw patient database 320. In the workflow 400, the process of extracting data from the incoming message 410 can include extracting data important for tracking patient movement (e.g., current patient location, current patient disposition, etc.) for storage in the event database 420. In implementation, if the incoming messages contain all of the fields necessary for both purposes, then the incoming message 310 and the incoming message 410 can be the same message or copies of the same message, which can include the same data or a shared resource. The portions of data that are extracted can be different according to different purposes for which they are used.

Based on the event data, patient-specific action tracking is performed to generate action data specific to one or more patients. The action data for each patient can include arrival time, roomed time, provider time, disposition time, admission time, discharge time, "left without being seen" ("LWBS") time, and/or absconded time. The action data can be stored in action database 430.

Based on the action data, a patient-specific duration calculation is performed to generate duration data specific to one or more patients. The duration data for each patient can include arrival-to-roomed, arrival-to-provider, roomed-to-provider, arrival-to-disposition, provider-to-disposition, arrival-to-admission, arrival-to-discharge, arrival-to-LWBS, and/or arrival-to-absconded. The duration data can be stored in duration database 440.

Based on the event data and/or the action data, current patient status tracking is performed to generate patient status data specific to one or more patients. The patient status data for each patient can include current location (bed, waiting room, etc.), current treatment team (A, B, C, etc.), and/or current status (waiting, triage, roomed, seen, etc.). The patient status data can be stored in patient status database 450.

At a given interval (e.g., 1 minute) and based on the status data, an overall status calculation is performed to generate overall status data for a set of patients. The overall status data for a set of patients can include patients in a waiting room, beds occupied, beds available, patients ready for admission, and/or patients ready for transport. The overall status data can be stored in overall status 470.

At a given interval (e.g., 1 minute) and based on the duration data and/or the overall status data, summary statistics calculation is performed to generate summary statistics data for each item or item category in duration database 440 and overall status database 470. The summary statistics data can include statistics for minimum value(s), maximum value(s), median value(s), overall value(s), value(s) for each treatment team, each shift, and/or for rolling (e.g., 8-hour and 24-hour) windows of time. The summary statistics data can be stored in summary statistics database 460.

The overall status data stored in overall status database 470 and the summary statistics data stored in summary statistics database 460 can be retrieved for display, use, and/or manipulation by a user interface 480. The user interface 480 can provide overall and patient-specific information to a user and/or other system components. The result of the workflow 300 (e.g., from the data store 340), can be a source of data for a user interface 480, in addition to data provided from summary statistics database 460 and/or overall status database 470, to include prediction data within the user interface 480 alongside current status information.

According to some embodiments, each of the event database 420, the action database 430, the duration database 440, the patient status database 450, the summary statistics database 460, and the overall status database 470 can be separate data stores to facilitate different processing of the data contained therein. As shown in FIG. 4, raw messages from the incoming messages 410 are processed and the relevant event data is extracted into the event database 420. Those events are then processed into event categories (e.g. "arrival", "disposition", "transfer", etc.) and stored in the action database 430. From this raw event data, durations, statuses, etc., can be calculated and stored in their own locations. Some locations are patient-specific, some are aggregated at a particular point in time, and some are aggregated for a given time period. All of these pieces of data drive the user interface 480.

Figure 5:
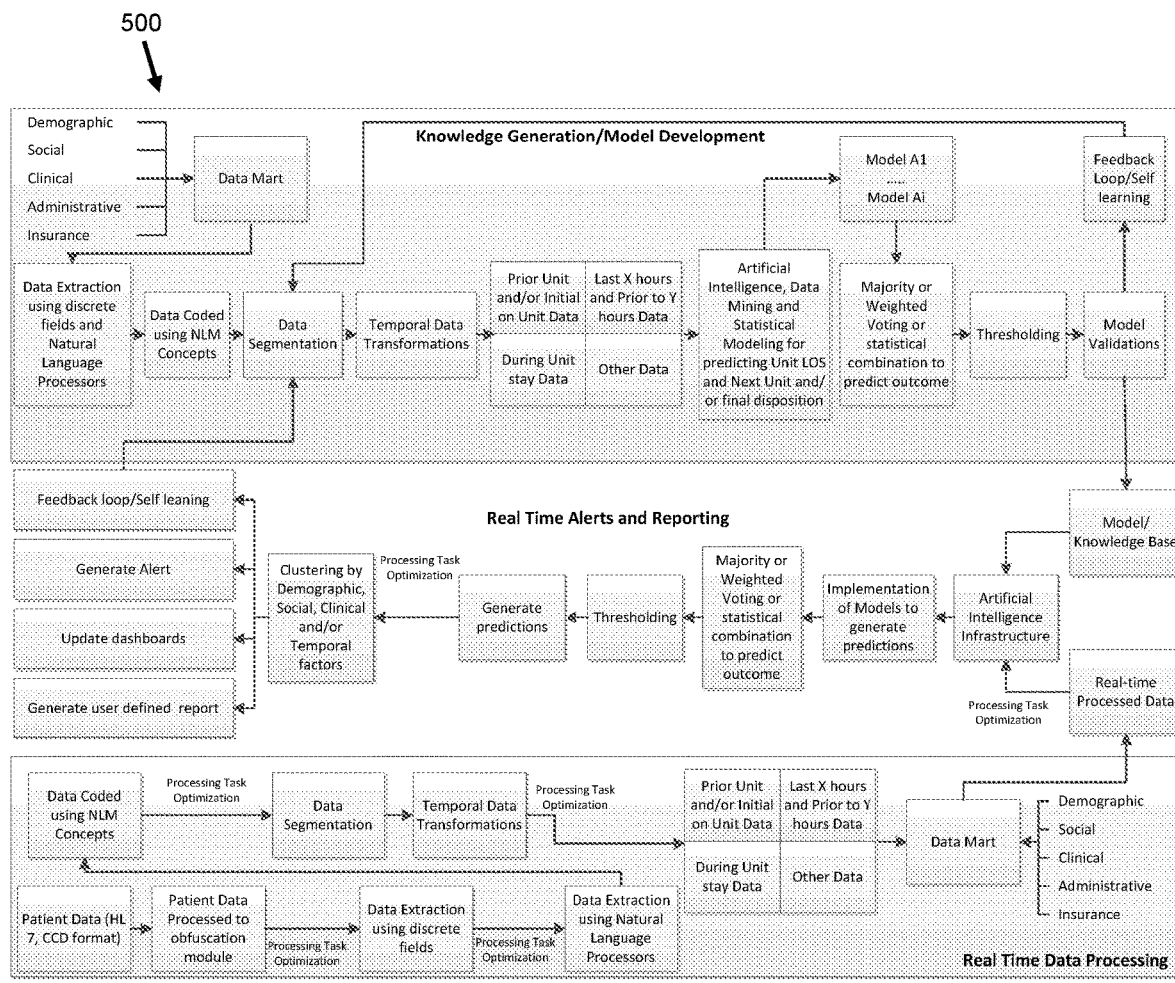
FIG. 5 illustrates an example workflow for predicting analytics relating to inpatient, emergency department ("ED"), and outpatient length-of-stay ("LOS") and location predictions, according to some embodiments of the subject technology.

The subject technology, in some embodiments, can predict length-of-stay ("LOS") and location predictions for a patient. For example, FIG. 5 illustrates an example workflow 500 for predicting analytics relating to inpatient, emergency department ("ED"), and outpatient length-of-stay ("LOS") and location predictions. As shown, the workflow 500 includes stages for "Data Segmentation," "Temporal Data Transformations," "Majority or Weighted Voting or statistical combination to predict outcome," and "Thresholding." Additional details for these stages are provided below. As further shown in FIG. 5, various stages include a steps of "Processing Task Optimization," in which data to be processed is, at such a point in the workflow 500, stored in a database-backed, priority-based queue. Items in the queue are assigned weight using a weighted first-in-first-out approach. Accordingly, priority within the queue is based upon the metadata of the items stored within the system. This facilitates optimal, near-real-time processing of all components within the workflow 500.

Figure 6:
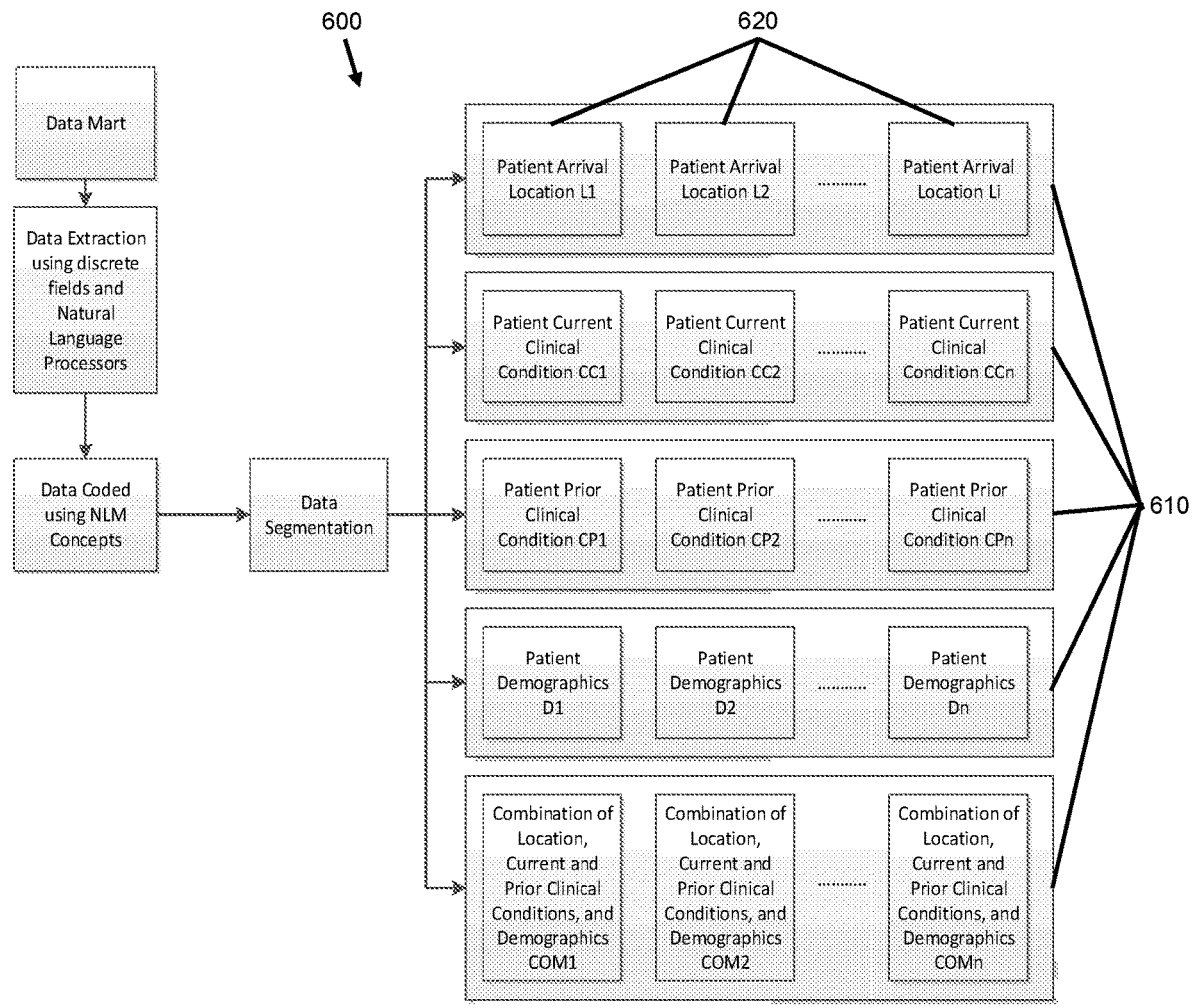
FIG. 6 illustrates an example data segmentation workflow for segmenting patient data, according to some embodiments of the subject technology.

The subject technology, in some embodiments, can utilize multiple data segments based on need, complexity of the underlying clinical conditions, and related predictions. For example, FIG. 6 illustrates an example data segmentation workflow 600 for segmenting patient data. Based on incoming data, extraction can be performed using discrete fields of the natural language processors. For example, the data can be coded using National Library of Medicine ("NLM") concepts and/or other libraries selected based on applicable fields and languages. The resulting data is segmented into categories that can include arrival location, current clinical condition, prior clinical condition, demographics, and/or combinations thereof. According to some embodiments, the data is segmented according to its kind and based on how it is used within the prediction operations. The segmented data segmented data can include a plurality of time series 610. Each of the time series 610 can include a plurality of conditions 620 of the patient across a period of time within the corresponding time series 610. For example, if a patient has 12 different readings of "fever" (e.g., 8 measured temperatures, I selected as the primary chief complaint, and 3 noted within the review of systems and past medical history), then all 12 of those readings are segmented into a single time series, which is distinct from a "blood pressure" time series, etc.

Figure 7:
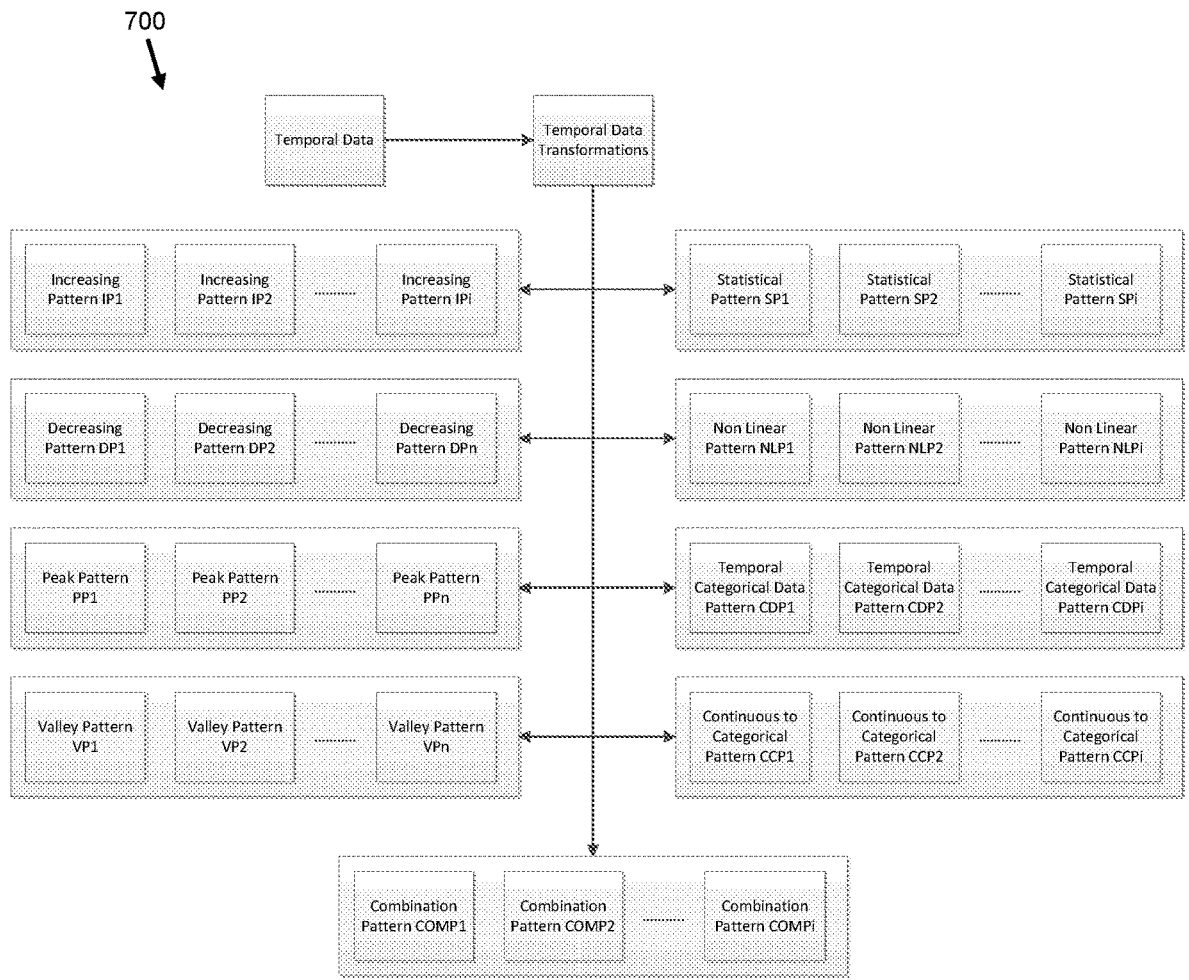
FIG. 7 illustrates an example temporal data transformation workflow, according to some embodiments of the subject technology.

The subject technology, in some embodiments, can perform temporal data transformations. For example, FIG. 7 illustrates an example temporal data transformation workflow 700. Data transformations can be used to accurately model complex systems within simplified statistical models. The temporal data can be transformed to generate new data based on one or more patterns, including increasing patterns, decreasing patterns, peak patterns, valley patterns, statistical patterns, nonlinear patterns, temporal categorical data patterns, continuous to categorical patterns, and/or combinations thereof. Examples of temporal data can include lab results (e.g., WBCs, potassium levels, etc.), vital signs (e.g., temperature, pulse, etc.), patient status (e.g., acuity levels, etc.), radiology results (e.g., CT scans), among others. The data segmentation described herein can be utilized for multiple prediction models to capture unique location, diseases, and other specific characteristics of underlying patient populations. All data can be timestamped, so each segment of data is essentially a time series of related readings. Based on the type of data, it will be aggregated in different ways. For example, only one "mode of arrival" may be expected, so if the data contains multiple modes of arrival, it can be inferred that the original was updated by staff, so the most recent can be used. By further example, with vital signs, the overall time series (e.g., minimum, maximum, trend) is significant. Any new data can be appended to the visit instance of the patient and stored in the raw patient database 320. For example, if a new temperature reading is added to the "fever" segment which also increases the maximum temperature, a new value would be added to the "maximum fever" segment, but not the "minimum fever" segment, which are both computed segments and not directly extracted from the incoming data.

According to some embodiments, a single variable can be transformed in a data transformation. For example, a nominal or continuous variable can be converted into a categorical variable. By further example, a function can be executed on a continuous variable to change its scale or orientation (e.g. exponentiation, logarithms, etc.).

According to some embodiments, multiple variables can be combined in a data transformation. For example, novel variables can be created by combining the values of multiple existing variables through weighted voting, thresholding, logical operations, fully connected conditional probability tables, etc. By further example, variables can be combined through statistical methods or by using expert clinical insight and guidance.

According to some embodiments, the coordinate system can be transformed in a data transformation. For example, the scale and orientation of all variables within a model can be changed using a coordinate system transformation (e.g. radial basis function, Gaussian kernel function, Cartesian to polar coordinate transformation, etc.).

According to some embodiments, the selected data transformation can be based on multiple aspects such as clinical conditions, statistical prediction model performance metrics, type and frequency of data availability, relative importance of the variable/data, among others. The data transformation selection process could be optimized through iterative applications of various transformations and selection of highest performing transformation with respect to the prediction model performance metrics. Due to the nature of some data elements along with clinically observed patterns, only certain transformations will be applied. Systems described herein can include a library of data elements and applicable transformations for ease for implementation.

Figure 8:
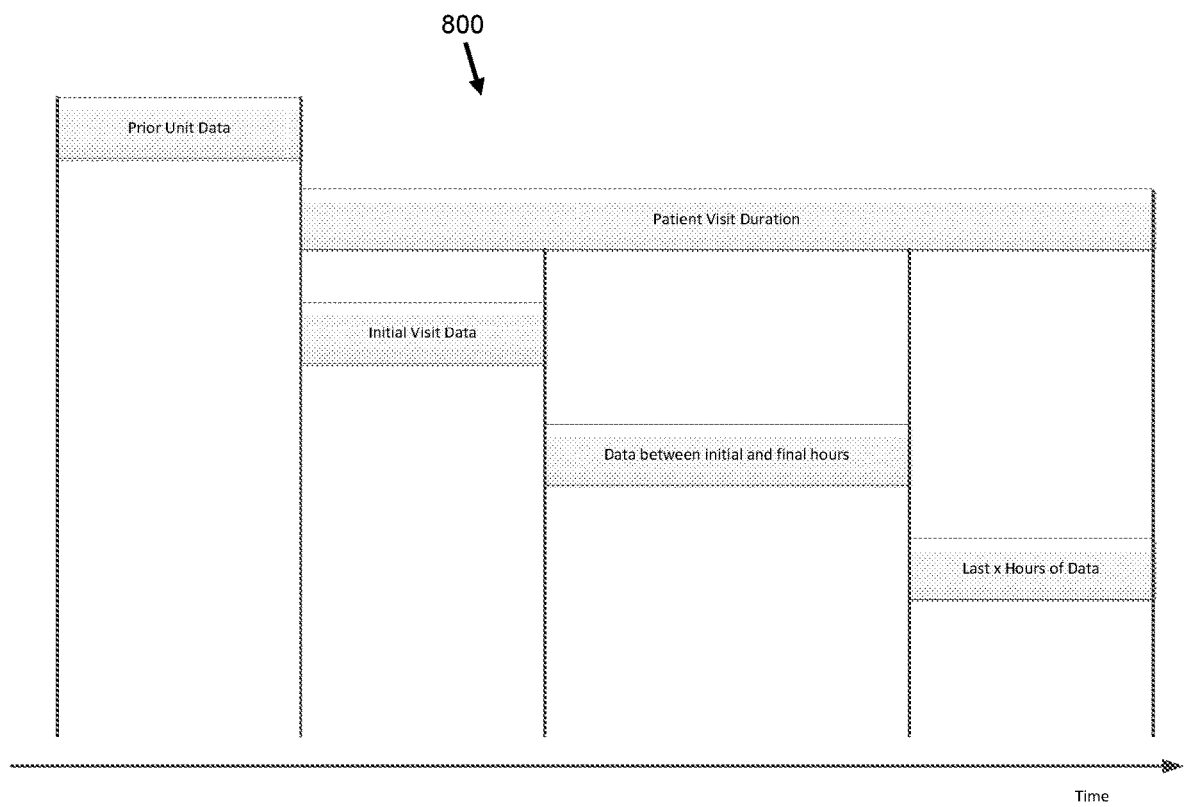
FIG. 8 illustrates an example record of spliced data, according to some embodiments of the subject technology.

FIG. 8 illustrates data that is provided at various stages with respect to the duration of a patient's visit. As shown, prior unit data can be generated prior to the beginning of a patient's visit. At the beginning of the patient's visit, initial visit data can be provided. For example, initial visit data can include information received from the patient during an admission process. Data between the initial and final hours of the visit can be provided. For example, supplemental information can be received, as well as updates regarding the patient's condition, treatment, and/or response to treatment. Finally, data can be provided during the last hours of the patient's visit. For example, information can be collected during a procedure for discharging the patient.

The data can be spliced based on when, during the patient encounter, it is coming from. According to some embodiments, a prediction model provides different weights to data from major time periods (e.g., pre-visit, early-visit, mid-visit, late-visit). For example, a high temperature on arrival to the ED is not as significant for predicting admission and admission duration as a high temperature near the end of an ED stay.

The incoming data can be continuous. However, for building the prediction models and implementing them, particular portions of the data can be utilized. These sections represent when and how early the predictions can be compiled. According to some embodiments, the first 8 hours of inpatient data can be used to build a model that predicts the total LOS as well as a final disposition. This information can assist the clinicians as well as administrators to provide optimal treatment as well as plan for the discharge and arrange for any necessary patient support system. According to some embodiments, the last 24 hours of data could be used to generate a report of predicted discharges in next 24 hours. This information can provide short term but reliable predictions that can be used for informing the discharge conversations, communications between various clinical and non-clinical providers, and communications with patients and their families. The subject technology, in some embodiments, can apply one or more models to predict the pathway and/or LOS of one or more patients. For example, multiple statistical models can be applied based on different outcomes, different independent variables, and the timing of the readings.

According to some embodiments, one or more decisions $Y_{jk}$ can be defined based on different models, j, different variables, i, and different readings, k, as shown below:

$$\text{Decision } Y_{jk} = \beta_{0jk} + \sum_{k=0}^{k}\sum_{i=0}^{i} \beta_{ik} * X_{ik}$$

for j=0 to j; k=0 to k, where $\beta_{ojk}$ and $\beta_{ik}$ are beta coefficients, and where $X_{ik}$ is for values of independent variables (for j different models using i different variable and k different readings)

$\beta_{ojk}$ and $\beta_{ik}$ are coefficients of a linear regression model which is applied to the normalized/categorized data values represented by $X_{ik}$. Other models (e.g. logistic regression, neural networks, etc.) would have different fundamental formulas but can also be applied for use. The decisions can be continuous, categorical, nominal, or binary. The models can be built using linear regression, generalized linear models, general linear models, logistic regression, and multinomial logistic regression among others.

According to some embodiments, a first data mining model can be used to determine a LOS category for a patient. Based on each of a number of patterns, a result can be determined. As described herein, the data transformations can create derived independent variables. The raw/original variables in combination with the derived variables will be used to create predictive models. Data mining models can create knowledge in form of patterns (see "Artificial Intelligence, Data Mining and Statistical Modeling for predicting Unit LOS and Next Unit and/or Final disposition" in the workflow 500 of FIG. 5). According to some embodiments, for each Pattern ijk, the following logic can apply:

IF Xijk Meets Condition AND/OR Xijk Meets Condition AND/OR . . . AND/OR Xijk Meets Condition then Decision ik=LOS Category M, for i=0 to i; j=0 to j; and k=0 to k (i.e., j different patterns using i different variables with k different readings). An example set of patterns are provided below:

Pattern 1: If Variable A=A3 AND Variable B<=B2 . . . AND Variable S=S1 or S4 then Decision=LOS Category I Pattern 2: If Variable E>=E2 AND Variable B<=B4 . . . AND Variable K=K5 then Decision=LOS Category III Pattern 3: If Variable D=D5 AND Variable C<=C1 . . . AND Variable Z between Z3 and Z6 then Decision=LOS Category II

. . .

Pattern n: If (Variable G=G3 OR Variable H<=H2) AND Variable D=D3 AND Variable C>=C3 . . . AND Variable S=S2 or S3 then Decision=LOS Category IV By further example, an example pattern is provided below:

IF age>55 AND Acuity=2 AND (Average pulse within last 4 hours between 90 and 110 OR SP02 is <90% OR First Respiration reading>25) THEN Decision=LOS Category 1 (8 days<LOS<6 days)

The results from the first data mining model according to each Pattern ijk can be generated and stored, as described herein. A second data mining model can be used to determine a "next unit" category for the patient. The determination of a next unit can indicate whether a patient is to be admitted, discharged, or otherwise directed to a location within the hospital. Based on each of a number of patterns, a result can be determined. For example, for each Pattern ijk, the following logic can apply:

IF Xijk Meets Condition AND/OR Xijk Meets Condition AND/OR . . . AND/OR Xijk Meets Condition then Decision ik=Next Location Unit U, for i=0 to i; j=0 to j; and k=0 to k (i.e., j different patterns using i different variables with k different readings). An example set of patterns are provided below:

Pattern 1: If Variable D=D2 AND Variable B<=B2 . . . AND Variable K=K1 or K4 then Decision=Next Unit M Pattern 2: If Variable E>=E2 AND Variable B<=B4 . . . AND Variable K=K5 then Decision=Next Unit J Pattern 3: If Variable D=D5 AND Variable C<=C1 . . . AND Variable Z between Z3 and Z6 then Decision=Next Unit D

. . .

Pattern n: If (Variable G=G3 OR Variable H<=H2) AND Variable D=D3 AND Variable C>=C3 . . . AND Variable S=S2 or S3 then Decision=Next Unit V The results from the second data mining model according to each pattern ijk can be generated and stored, as described herein.

According to some embodiments, multiple Bayesian network models can be constructed for each different decision and expressed as:

$$Pr(x_1, x_2, \ldots, x_n) = \prod_{i=1}^{n} Pr(x_i \mid \text{Parents}(X_i))$$

where $\text{Parents}(X_i) \subseteq (X_1, \ldots, X_{i-1})$

Decisions can be modeled as either binary or categorical. Nominal or continuous decisions are converted into categorical decisions using thresholds prior to model building and application. Assignment of parents is based on observed conditional independence, D-separation within the directed acyclic graph nodes, causal sufficiency assumptions, domain expert feedback, or a combination of these factors. Additional graph topology optimization can occur after initial assignment of parents using Markov blanket covering or similar algorithms in order to improve the accuracy and confidence of the initial topology. Conditional probability tables for each node within the graph are based on historical data, literature-derived values or a combination of both. Feedback and additional information can be incorporated within the Bayesian network to improve accuracy either through changes to the structure or the conditional probability tables, or both.

According to some embodiments, the multiple decisions can be combined to produce a final decision. For example, the decisions can be subjected to a voting scheme, weighted voting scheme, or a statistical combination. Multiple models of the same or different statistical types for the same outcome can be statistically combined to yield a final decision/outcome. Each model's individual outcome receives a single vote or its vote is weighted based on its prediction confidence, tuning-based bagging/boosting coefficients, or a predefined weighting scheme. Multiple outcomes/models can also be combined stochastically using Monte Carlo simulations to provide additional weighting among outcomes. The decision/outcome with the highest overall votes/score will be selected as the final decision. For example, the Final Decision Y can be expressed as:

$$\text{Final Decision } Y = \text{MAX or MIN}\left(\sum_{s=0}^{s} W_s * Y_s', \sum_{t=0}^{t} W_t * Y_t \ldots \sum_{x=0}^{x} W_x * Y_x\right)$$

According to some embodiments, the decision(s) can be processed with thresholding. To reduce noise within the data, various thresholding approaches can be employed. Decisions can be made only if a certain level of confidence is achieved. For example, if a predicted confidence is greater than or equal to a threshold, then the final decision is the prediction value. Otherwise, the decision can be unknown or additional information can be required. Thresholds can be determined based on balancing statistical performance metrics as well as clinical inputs and can be unique for each model per application. Thresholds can be determined using one or more of (1) Gaussian denormalization of historical data to determine the intersections of existing normal distributions within the data, (2) calculation of confidence intervals for each possible decision/outcome, and (3) expert review of the tradeoff between Type I and Type II errors using Receiver Operating Characteristic (ROC) curves and/or Precision Recall Curves (PRC).

According to some embodiments, additional data can be added to refine the models and improve statistical performance metrics as well a clinical interpretability and operational ability. Feedback and additional information will be incorporated within each model and within the final decision algorithm in order to improve accuracy, either through changes to the structure of the model(s) and/or the values associated with the model(s). Additional data can be data that is not utilized in the current model but can be added. The additional data can be already available in the current data feeds (e.g., WBC available but not used in the current model). The additional data can be new data fields added due to clinical and operational reasons (e.g., adding travel to specific regions for say ebola/zika monitoring, socioeconomic data points such as home support, etc.). The additional data can be newly derived variables due to temporal transformations.

According to some embodiments, workflows can be specifically tailored to track and predict pathways for ED patients, OR/surgical patients, and/or outpatient/other patients. Aspects discussed above, such as data segmentation, temporal data transformations, visit segments, prediction models, majority or weighted voting or statistical combination to predict outcome, and thresholding, among others, can be applied to ED workflows, OR/surgical workflows, and/or outpatient/other patient workflows. According to some embodiments, aspects of these workflows can be similar to the workflow 500 shown in FIG. 5 and described above. Accordingly, these aspects are not repeated for each of the workflows described below.

Figure 9:
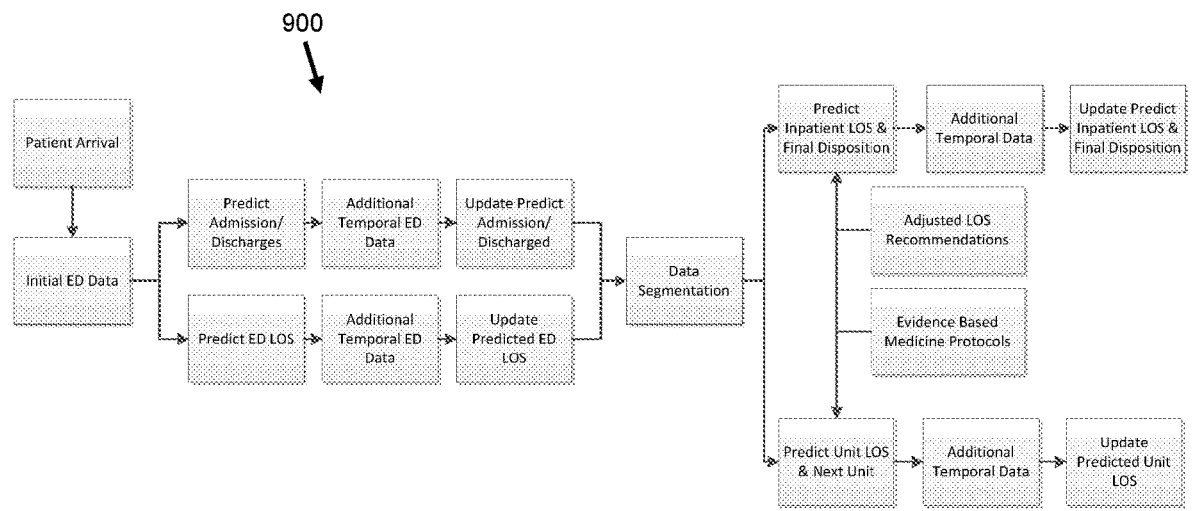
FIG. 9 illustrates an example workflow for tracking and predicting LOS and location for patients entering a hospital at an emergency department, according to some embodiments of the subject technology.

FIG. 9 illustrates an ED workflow 900 for tracking and predicting LOS and location for patients entering a hospital at an emergency department.

Figure 10:
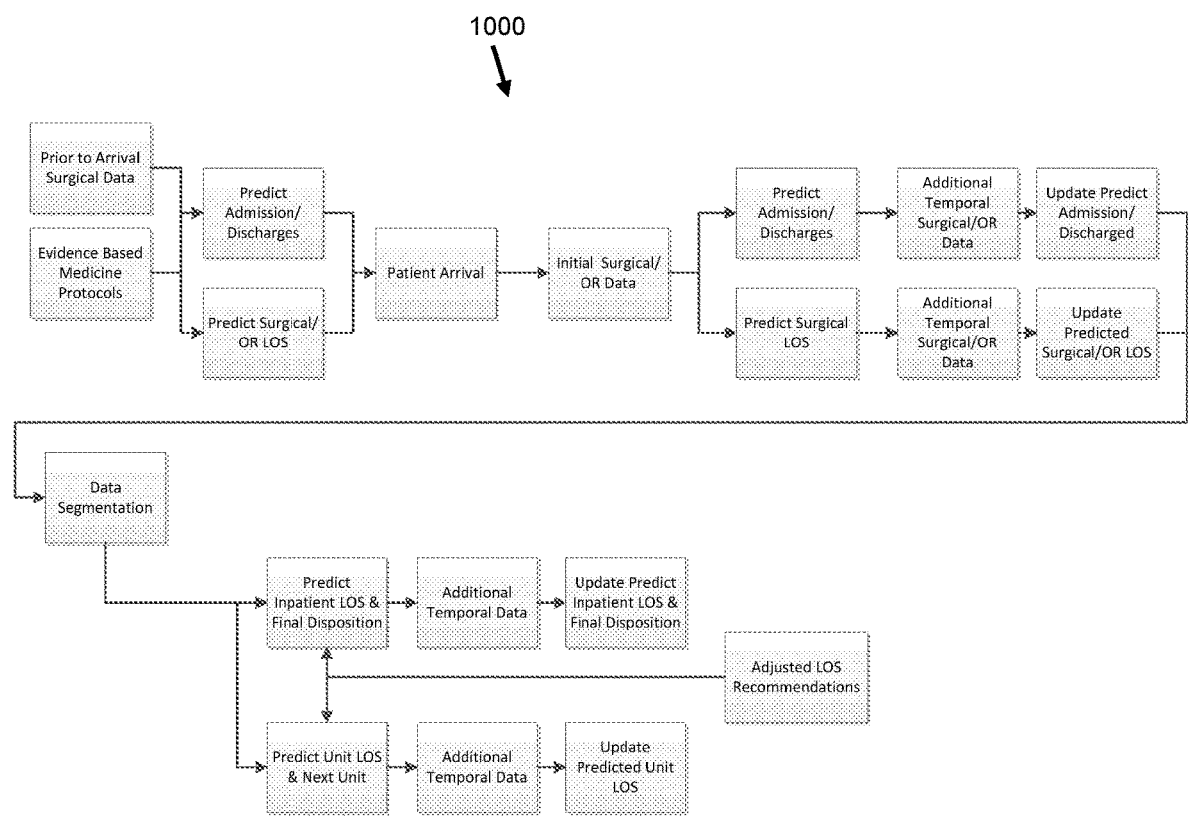
FIG. 10 illustrates an example workflow for tracking and predicting LOS and location for patients entering a hospital for scheduled visitation to an OR/surgical department, according to some embodiments of the subject technology.

FIG. 10 illustrates an OR/surgical workflow 1000 for tracking and predicting LOS and location for patients entering a hospital for scheduled visitation to an OR/surgical department.

Figure 11:
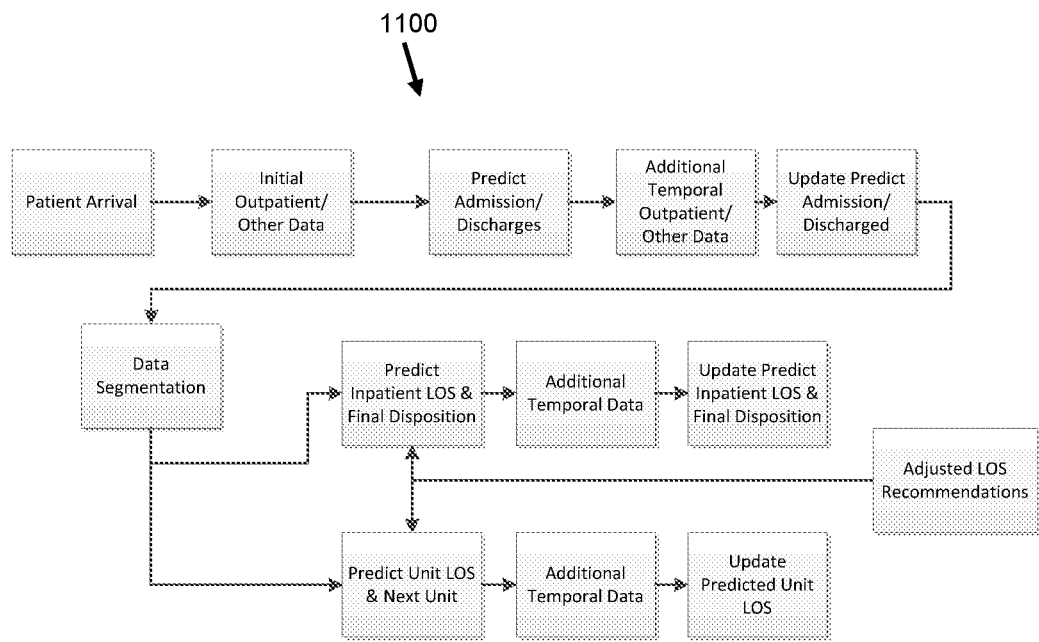
FIG. 11 illustrates an example workflow for tracking and predicting LOS and location for patients entering a hospital for scheduled outpatient or other procedures, according to some embodiments of the subject technology.

FIG. 11 illustrates an outpatient/other patient workflow 1100 for tracking and predicting LOS and location for patients entering a hospital for scheduled outpatient or other procedures.

According to some embodiments, the workflows 900, 1000, and/or 1100 can include multiple sets of data segmentation. The first set of data segmentation can be based on initial data, which may have limited information for data segmentations. For example, chief complaint in the ED are subject to change and could be different than final ED diagnosis. Thus, initial data segmentation may utilize a limited number of aspects while the subsequent data segmentation after completing the ED, OR, and/or outpatient visits will utilize more reliable information. In addition, the first set of predictions can be used for setting specific operations such as ED, OR, and/or outpatient. The goal of these predictions can be either to admit or discharge the patients after completing the visit in that setting as well as estimating the expected LOS in the respective settings. According to some embodiments, if the initial data in the ED is limited, no data segmentations may be performed. While as the initial OR data will have more reliable information than ED, data segmentation can be applied prior to initial predictions. Thus, two levels of data segmentation can be used (e.g., initial limited data based segmentation and regular data segmentation).

Figure 12:
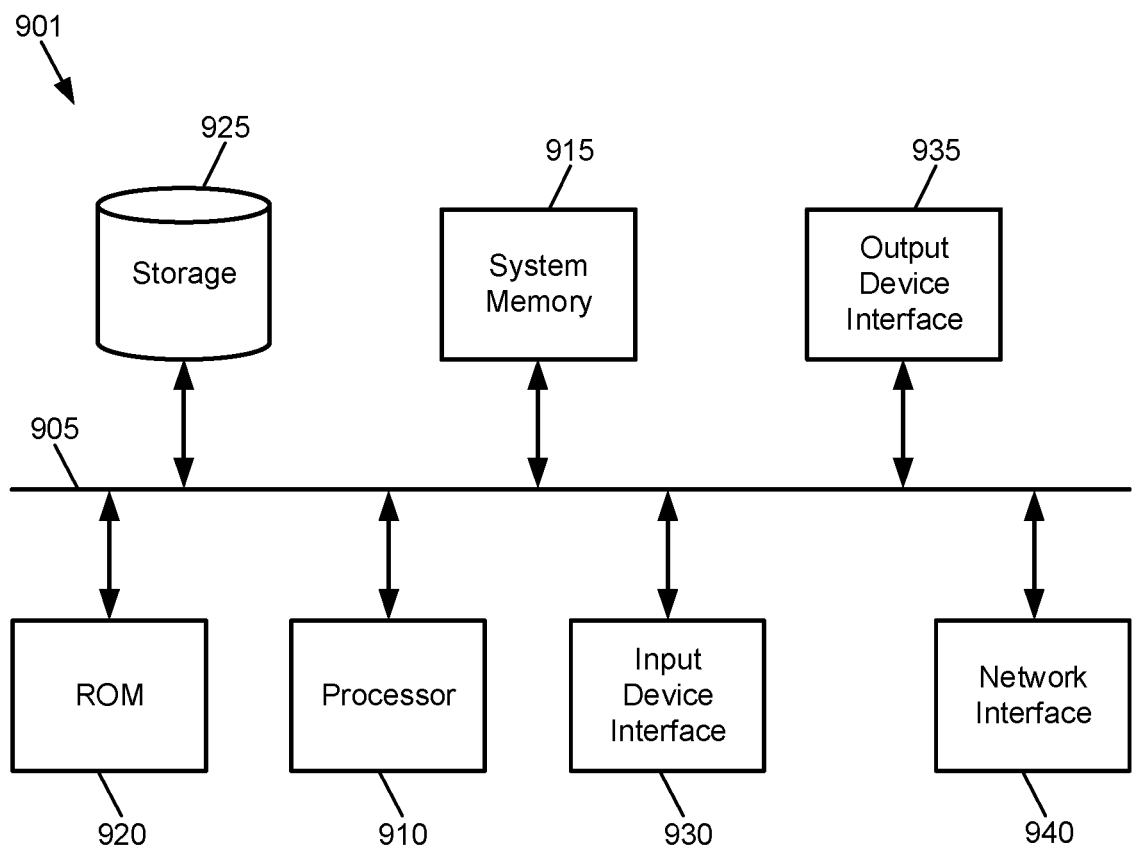
FIG. 12 conceptually illustrates an example electronic system, according to some embodiments of the subject technology.

FIG. 12 conceptually illustrates an electronic system 901 with which some implementations of the subject technology are implemented. For example, one or more of the systems described above may be implemented using the arrangement of the electronic system 901. The electronic system 901 can be a computer (e.g., a mobile phone, PDA), or any other sort of electronic device. Such an electronic system includes various types of computer readable media and interfaces for various other types of computer readable media. Electronic system 901 includes a bus 905, a processor or processing unit 910, a system memory 915, a read-only memory 920, a permanent storage device 925, an input device interface 930, an output device interface 935, and a network interface 940.

The bus 905 collectively represents all system, peripheral, and chipset buses that communicatively connect the numerous internal devices of the electronic system 901. For instance, the bus 905 communicatively connects the processing unit(s) 910 with the read-only memory 920, the system memory 915, and the permanent storage device 925.

From these various memory units, the processing unit(s) 910 retrieves instructions to execute and data to process in order to execute the processes of the subject technology. The processing unit(s) can be a single processor or a multi-core processor in different implementations.

The read-only-memory (ROM) 920 stores static data and instructions that are needed by the processing unit(s) 910 and other modules of the electronic system. The permanent storage device 925, on the other hand, is a read-and-write memory device. This device is a non-volatile memory unit that stores instructions and data even when the electronic system 901 is off. Some implementations of the subject technology use a mass-storage device (for example, a magnetic or optical disk and its corresponding disk drive) as the permanent storage device 925.

Other implementations use a removable storage device (for example a floppy disk, flash drive, and its corresponding disk drive) as the permanent storage device 925. Like the permanent storage device 925, the system memory 915 is a read-and-write memory device. However, unlike storage device 925, the system memory 915 is a volatile read-and-write memory, such a random access memory. The system memory 915 stores some of the instructions and data that the processor needs at runtime. In some implementations, the processes of the subject technology are stored in the system memory 915, the permanent storage device 925, or the read-only memory 920. For example, the various memory units include instructions for generating a diagnosis or detecting an outbreak of a medical condition in accordance with some implementations. From these various memory units, the processing unites) 910 retrieves instructions to execute and data to process in order to execute the processes of some implementations.

The bus 905 also connects to the input and output device interfaces 930 and 935. The input device interface 930 enables the user to communicate information and select commands to the electronic system. Input devices used with input device interface 930 include, for example, alphanumeric keyboards and pointing devices (also called "cursor control devices"). Output device interfaces 935 enables, for example, the display of images generated by the electronic system 901. Output devices used with output device interface 935 include, for example, printers and display devices, for example, cathode ray tubes (CRT) or liquid crystal displays (LCD). Some implementations include devices for example a touch screen that functions as both input and output devices.

Finally, as shown in FIG. 12, bus 905 also couples electronic system 901 to a network (not shown) through a network interface 940. In this manner, the electronic system 901 can be a part of a network of computers (for example a local area network (LAN), a wide area network (WAN), or an Intranet, or a network of networks, for example the Internet. Any or all components of electronic system 901 can be used in conjunction with the subject technology.

The above-described features and applications can be implemented as software processes that are specified as a set of instructions recorded on a computer readable storage medium (also referred to as computer readable medium). When these instructions are executed by one or more processing unites) (e.g., one or more processors, cores of processors, or other processing units), they cause the processing unites) to perform the actions indicated in the instructions. Examples of computer readable media include, but are not limited to, CD-ROMs, flash drives, RAM chips, hard drives, EPROMs, etc. The computer readable media does not include carrier waves and electronic signals passing wirelessly or over wired connections.

In this specification, the term "software" is meant to include firmware residing in read-only memory or applications stored in magnetic storage or flash storage, for example, a solid-state drive, which can be read into memory for processing by a processor. In addition, in some implementations, multiple software technologies can be implemented as sub-parts of a larger program while remaining distinct software technologies. In some implementations, multiple software technologies can also be implemented as separate programs. Finally, any combination of separate programs that together implement a software technology described here is within the scope of the subject technology. In some implementations, the software programs, when installed to operate on one or more electronic systems, define one or more specific machine implementations that execute and perform the operations of the software programs.

A computer program (also known as a program, software, software application, script, or code) can be written in any form of programming language, including compiled or interpreted languages, declarative or procedural languages, and it can be deployed in any form, including as a standalone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

These functions described above can be implemented in digital electronic circuitry, in computer software, firmware or hardware. The techniques can be implemented using one or more computer program products. Programmable processors and computers can be included in or packaged as mobile devices. The processes and logic flows can be performed by one or more programmable processors and by one or more programmable logic circuitry. General and special purpose computing devices and storage devices can be interconnected through communication networks.

Some implementations include electronic components, for example, microprocessors, storage and memory that store computer program instructions in a machine readable or computer-readable medium (alternatively referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic or solid state hard drives, read-only and recordable Blu-Ray® discs, ultra-density optical discs, any other optical or magnetic media, and floppy disks. The computer-readable media can store a computer program that is executable by at least one processing unit and includes sets of instructions for performing various operations. Examples of computer programs or computer code include machine code, for example as produced by a compiler, and files including higher-level code that are executed by a computer, an electronic component, or a microprocessor using an interpreter.

While the above discussion primarily refers to microprocessor or multi-core processors that execute software, some implementations are performed by one or more integrated circuits, for example application specific integrated circuits (ASICs) or field programmable gate arrays (FPGAs). In some implementations, such integrated circuits execute instructions that are stored on the circuit itself.

As used in this specification and any claims of this application, the terms "computer", "server", "processor", and "memory" all refer to electronic or other technological devices. These terms exclude people or groups of people. For the purposes of the specification, the terms display or displaying means displaying on an electronic device. As used in this specification and any claims of this application, the terms "computer readable medium" and "computer readable media" are entirely restricted to tangible, physical objects that store information in a form that is readable by a computer. These terms exclude any wireless signals, wired download signals, and any other ephemeral signals.

To provide for interaction with a user, implementations of the subject matter described in this specification can be implemented on a computer having a display device, e.g., a cathode ray tube (CRT) or liquid crystal display (LCD) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

The subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network (LAN) and a wide area network (WAN), an inter-network (e.g., the Internet), and peer-to-peer networks (e.g., ad hoc peer-to-peer networks).

The computing system can include clients and servers. A client and server are generally remote from each other and typically interact through a communication network. The relationship of client and server arises by virtue of computer programs running on the respective computers and having a client-server relationship to each other. In some aspects of the disclosed subject matter, a server transmits data (e.g., an HTML page) to a client device (e.g., for purposes of displaying data to and receiving user input from a user interacting with the client device). Data generated at the client device (e.g., a result of the user interaction) can be received from the client device at the server.

It is understood that any specific order or hierarchy of steps in the processes disclosed is an illustration of example approaches. Based upon design preferences, it is understood that the specific order or hierarchy of steps in the processes may be rearranged, or that all illustrated steps be performed. Some of the steps may be performed simultaneously. For example, in certain circumstances, multitasking and parallel processing may be advantageous. Moreover, the separation of various system components illustrated above should not be understood as requiring such separation, and it should be understood that the described program components and systems can generally be integrated together in a single software product or packaged into multiple software products.

Various modifications to these aspects will be readily apparent, and the generic principles defined herein may be applied to other aspects. Thus, the claims are not intended to be limited to the aspects shown herein, but is to be accorded the full scope consistent with the language claims, where reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the subject technology.

A phrase, for example, an "aspect" does not imply that the aspect is essential to the subject technology or that the aspect applies to all configurations of the subject technology. A disclosure relating to an aspect may apply to all configurations, or one or more configurations. A phrase, for example, an aspect may refer to one or more aspects and vice versa. A phrase, for example, a "configuration" does not imply that such configuration is essential to the subject technology or that such configuration applies to all configurations of the subject technology. A disclosure relating to a configuration may apply to all configurations, or one or more configurations. A phrase, for example, a configuration may refer to one or more configurations and vice versa.

What is claimed is:

1. A system for predicting patient admission and stay at a healthcare facility, the system comprising one or more processors;
   a raw patient database;
   a normalized and categorized patient database storing normalized and categorized data associated with each of a plurality of patients of the healthcare facility;
   a prediction database; and
   a memory in communication with the one or more processors, the memory storing instructions, wherein, when executed by the one or more processors, the instructions cause the one or more processors to:
   receive initial patient data associated with a patient;
   interpret, using natural language processing, the initial patient data;
   store the interpreted initial patient data in the raw patient database;
   extract, from the interpreted initial patient data, one or more conditions of the patient upon arrival to a first unit of the healthcare facility;
   categorize the extracted one or more conditions;
   store the categorized extracted one or more conditions as initial categorized patient data in the normalized and categorized patient database;
   generate, from the initial categorized patient data, a first prediction comprising a predicted characteristic of a patient stay at the first unit, wherein the first prediction is generated based on a selected decision of a plurality of decisions output from one or more data mining models, the selected decision being obtained using a threshold determined from a Gaussian denormalization of historical data, a calculation of confidence intervals for each of the plurality of decisions, and one or more clinical inputs;
   store the first prediction in the prediction database;
   receive additional patient data based on the patient stay at the first unit;
   interpret, using natural language processing, the additional patient data;
   store the interpreted additional patient data in the raw patient database;
   extract, from the interpreted additional patient data, one or more additional conditions of the patient upon discharge from the first unit;
   categorize the extracted additional one or more conditions;
   store the categorized extracted additional one or more conditions as additional categorized patient data in the normalized and categorized patient database;
   segment portions of the initial categorized patient data and the additional categorized patient data into segmented data, wherein the segmented data comprises a plurality of time series, each of the plurality of time series comprises a plurality of indicators for a condition of the patient across a period of time;
   build a second data mining model comprising a plurality of patterns based on the normalized and categorized data, each pattern defining a decision of a patient stay at a second unit of the healthcare facility as a function of one or more variables of the normalized and categorized data satisfying a given decision condition;
   generate, as a function of the segmented data and the second data mining model, a second prediction comprising a predicted characteristic of the patient stay at the second unit; and
   store the second prediction in the prediction database.

2. The system of claim 1, wherein generating the second prediction comprises comparing the segmented data to the plurality of patterns of the second data mining model.

3. The system of claim 1, wherein the characteristic of the patient stay at the first unit comprises an admit to the second unit prediction, a discharge prediction, a length-of-stay in the first unit prediction.

4. The system of claim 1, wherein the characteristic of the patient stay at the second unit comprises a length-of-stay in the second unit prediction, and/or a final disposition prediction.

5. The system of claim 1, wherein the condition of the patient comprises arrival location, clinical condition, and/or demographics data.

6. The system of claim 1, wherein generating the second prediction comprises:
   comparing the segmented data to patterns of a plurality of predictive models; and
   combining results of the comparing with majority or weighted voting or statistical combination.

7. The system of claim 1, wherein the instructions, when executed by one or more processors, cause the one or more processors to:
   after receiving the initial data, receive temporal data comprising variables relating to the patient;
   transform the temporal data into transformed data; and
   store the transformed data in one or more of a plurality of pattern categories.

8. The system of claim 7, wherein the transforming comprises:
   converting a variable of the temporal data into a categorical variable;
   changing a scale or orientation of the variable;
   combining multiple variables of the temporal data; and
   transforming a coordinate system of the temporal data.

9. A method for predicting patient admission and stay at a healthcare facility, the method comprising:
   receiving, by a device comprising at least one processor and at least one memory in communication with the at least one processor, initial patient data;
   interpreting, by the device and using natural language processing, the initial patient data;
   storing, by the device, the interpreted initial patient data associated with a patient in a raw patient database;
   extracting, by the device from the interpreted initial patient data, one or more conditions of the patient upon arrival to a first unit of the healthcare facility;
   categorizing, by the device, the extracted one or more conditions;
   storing, by the device, the categorized extracted one or more conditions as initial categorized patient data in a normalized and categorized patient database, wherein the normalized and categorized patient data stores normalized and categorized data associated with each of a plurality of patients of the healthcare facility;
   generating, by the device and from the initial categorized patient data, a first prediction comprising a predicted characteristic of a patient stay at the first unit, wherein the first prediction is generated based on a selected decision of a plurality of decisions output from one ro more data mining models, the selected decision being obtained using a threshold determined from a Gaussian denormalization of historical data, a calculation of confidence intervals for each of the plurality of decisions, and one or more clinical inputs;
   storing, by the device, the first prediction in a prediction database;

receiving, by the device, additional patient data based on the patient stay at the first unit;

interpreting, by the device and using natural language processing, the additional patient data:

storing, by the device, the interpreted additional patient data in the raw patient database;

extracting, by the device from the interpreted additional patient data, one or more conditions of the patient upon discharge from the first unit;

categorizing, by the device, the extracted additional one or more conditions;

storing, by the device, the categorized extracted additional one or more conditions as additional categorized patient data in a normalized and categorized patient database;

segmenting, by the device, portions of the initial categorized patient data and the additional categorized patient data into segmented data, wherein the segmented data comprises a plurality of time series, each of the plurality of time series comprises a plurality of indicators for a condition of the patient across a period of time;

building a second data mining model comprising a plurality of patterns based on the normalized and categorized data, each pattern defining a decision of a patient stay at a second unit of the healthcare facility as a function of one or more variables of the normalized and categorized data satisfying a given decision condition;

generating, by the device and as a function of the segmented data and the second data mining model, a second prediction comprising a predicted characteristic of a patient stay at the second unit; and storing, by the device, the second prediction in the prediction database.

10. The method of claim 9, wherein generating the second prediction comprises comparing, by the device, the segmented data to the plurality of patterns of the second data mining model.

11. The method of claim 9, wherein the characteristic of the patient stay at the first unit comprises an admit to the second unit prediction, a discharge prediction, a length-of-stay in the first unit prediction.

12. The method of claim 9, wherein the characteristic of the patient stay at the second unit comprises a length-of-stay in the second unit prediction, and/or a final disposition prediction.

13. The method of claim 9, wherein the condition of the patient comprises arrival location, clinical condition, and/or demographics data.

14. The method of claim 9, wherein generating the second prediction comprises:

comparing, by the device, the segmented data to patterns of a plurality of predictive models; and combining, by the device, results of the comparing with majority or weighted voting or statistical combination.

15. The method of claim 9, further comprising:

after receiving the initial data, receiving, by the device, temporal data comprising variables relating to the patient;

transforming, by the device, the temporal data into transformed data; and storing, by the device, the transformed data in one or more of a plurality of pattern categories.

16. The method of claim 15, wherein the transforming the temporal data into the transformed data comprises:

converting, by the device, a variable of the temporal data into a categorical variable;

changing, by the device, a scale or orientation of the variable;

combining, by the device, multiple variables of the temporal data; and transforming, by the device, a coordinate system of the temporal data.

17. A non-transitory computer-readable medium comprising instructions for predicting patient admission and stay at a healthcare facility which, when executed by one or more processors, cause the one or more processors to:

receive initial patient data associated with a patient;

interpret, using natural language processing, the initial patient data;

store the interpreted initial patient data in a raw patient database;

extract, from the interpreted initial patient data, one or more conditions of the patient upon arrival to a first unit of the healthcare facility;

categorize the extracted one or more conditions;

store the categorized extracted one or more conditions as initial categorized patient data in a normalized and categorized patient database, wherein the normalized and categorized patient data stores normalized and categorized data associated with each of a plurality of patients of the healthcare facility;

generate, from the initial categorized patient data, a first prediction comprising a predicted characteristic of a patient stay at the first unit, wherein the first prediction is generated based on a selected decision of a plurality of decisions output from one or more data mining models, the selected decision being obtained using a threshold determined from a Gaussian denormalization of historical data, a calculation of confidence intervals for each of the plurality of decisions, and one or more clinical inputs;

store the first prediction in a prediction database;

receive additional patient data based on the patient stay at the first unit;

interpreting, using natural language processing, the additional patient data;

store the interpreted additional patient data in the raw patient database;

extract, from the interpreted additional patient data, one or more conditions of the patient upon discharge from the first unit;

categorizing the extracted additional one or more conditions;

store the categorized extracted additional one or more conditions as additional categorized patient data in the normalized and categorized patient database;

segment portions of the initial categorized patient data and the additional categorized patient data into segmented data, wherein the segmented data comprises a plurality of time series, each of the plurality of time series comprises a plurality of indicators for a condition of the patient across a period of time;

build second a data mining model comprising a plurality of patterns based on the normalized and categorized data, each pattern defining a decision of a patient stay at a second unit of the healthcare facility as a function of one or more variables of the normalized and categorized data satisfying a given decision condition;

generate, as a function of the segmented data and the second data mining model, a second prediction comprising a predicted characteristic of a patient stay at the second unit; and store the second prediction in the prediction database.

18. The non-transitory computer-readable medium of claim 17, wherein generating the second prediction comprises comparing the segmented data to the plurality of patterns of the second data mining model.

19. The non-transitory computer-readable medium of claim 17, wherein the characteristic of the patient stay at the first unit comprises an admit to the second unit prediction, a discharge prediction, a length-of-stay in the first unit prediction.

20. The non-transitory computer-readable medium of claim 17, wherein the characteristic of the patient stay at the second unit comprises a length-of-stay in the second unit prediction, and/or a final disposition prediction.

21. The non-transitory computer-readable medium of claim 17, wherein the condition of the patient comprises arrival location, clinical condition, and/or demographics data.

22. The non-transitory computer-readable medium of claim 17, wherein generating the second prediction comprises:
   comparing the segmented data to patterns of a plurality of predictive models; and
   combining results of the comparing with majority or weighted voting or statistical combination.

23. The non-transitory computer-readable medium of claim 17, wherein the instructions, when executed by the one or more processors, further cause the one or more processors to:
   after receiving the initial data, receive temporal data comprising variables relating to the patient;
   transform the temporal data into transformed data; and
   store the transformed data in one or more of a plurality of pattern categories.

24. The non-transitory computer-readable medium of claim 23, wherein when the instructions cause the one or more processors to transform the temporal data into the transformed data, the instructions cause the one or more processors to:
   convert a variable of the temporal data into a categorical variable;
   change a scale or orientation of the variable;
   combine multiple variables of the temporal data; and
   transform a coordinate system of the temporal data.

* * * * *